United States Patent
Gholipour-Baboli et al.

(10) Patent No.: US 10,403,007 B2
(45) Date of Patent: Sep. 3, 2019

(54) REGISTRATION-BASED MOTION TRACKING FOR MOTION-ROBUST IMAGING

(71) Applicant: Children's Medical Center Corporation, Boston, MA (US)

(72) Inventors: Ali Gholipour-Baboli, Quincy, MA (US); Bahram Marami, Brookline, MA (US); Simon K. Warfield, Brookline, MA (US); Benoit Scherrer, Somerville, MA (US); Onur Afacan, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 137 days.

(21) Appl. No.: 15/490,321

(22) Filed: Apr. 18, 2017

(65) Prior Publication Data
US 2018/0260981 A1    Sep. 13, 2018

Related U.S. Application Data (60) Provisional application No. 62/468,087, filed on Mar. 7, 2017.

(51) Int. Cl.
*G06T 11/00* (2006.01)
*A61B 5/055* (2006.01)

(52) U.S. Cl.
CPC ............ *G06T 11/003* (2013.01); *A61B 5/055* (2013.01); *G06T 2210/41* (2013.01)

(58) Field of Classification Search
CPC ......................... G06T 11/003; G06T 2210/41
See application file for complete search history.

(56) References Cited

U.S. PATENT DOCUMENTS

| | | | | |
|---|---|---|---|---|
| 6,980,001 B2 * | 12/2005 | Paley | ................... | G01R 33/445 324/318 |
| 9,202,272 B2 * | 12/2015 | Akcakaya | ............. | G06T 7/0012 |
| 2005/0238254 A1 * | 10/2005 | Guhring | ................ | G06T 3/0075 382/294 |
| 2014/0210469 A1 * | 7/2014 | Cheng | ............... | G01R 33/56509 324/309 |

(Continued)

OTHER PUBLICATIONS

Marami, Bahram, et al. "Elastic registration of prostate MR images based on estimation of deformation states." Medical image analysis 21.1 (2015): 87-103. (Year: 2015).*

(Continued)

*Primary Examiner* — Jonathan S Lee
(74) *Attorney, Agent, or Firm* — Wolf, Greenfield & Sacks, P.C.

(57) ABSTRACT

System and method for processing magnetic resonance imaging (MRI) data of an object to perform motion correction. The method comprises estimating, for each slice of the MRI data, parameters for a state space model using a filter that predicts the location of the object for temporally adjacent slices, wherein the state space model represents motion dynamics of the object throughout acquisition of a three-dimensional volume, registering the slices to a reference image based, at least in part, on the estimated parameters, reconstructing an image based, at least in part, on the registered two-dimensional slices, and outputting the reconstructed image.

17 Claims, 3 Drawing Sheets

(56) References Cited

U.S. PATENT DOCUMENTS

2016/0192889 A1* 7/2016 Koutsouleris .......... G16H 50/30
600/410

OTHER PUBLICATIONS

Li, Yue, et al. "Image corruption detection in diffusion tensor imaging for post-processing and real-time monitoring." PloS one 8.10 (2013): e49764. (Year: 2013).*
Chen et al., Particle Filtering for Slice-to-Volume Motion Correction in EPI Based Functional MRI. IEEE. 2016. 5 pages.
Marami et al., Motion-Robust Diffusion-Weighted Brain MRI Reconstruction Through Slice-Level Registration-Based Motion Tracking. IEEE Transactions on Medical Imaging. 2016;35(10):2258-69.
Marami et al., Motion-Robust Reconstruction Based on Simultaneous Multi-slice Registration for Diffusion-Weighted MRI of Moving Subjects. Springer International. 2016. 9 pages.

* cited by examiner

REGISTRATION-BASED MOTION TRACKING FOR MOTION-ROBUST IMAGING

RELATED APPLICATIONS

The present application claims the benefit under 35 U.S.C. § 119(e) of U.S. Provisional Patent Application No. 62/468,087, filed Mar. 7, 2017, titled "Registration-Based Motion Tracking for Motion-Robust Imaging," which is hereby incorporated by reference in its entirety.

FEDERALLY SPONSORED RESEARCH

This invention was made with government support under grant numbers EB018988, EB019483, and EB013248 awarded by the National Institutes of Health. The Government has certain rights in the invention.

BACKGROUND

Magnetic resonance imaging (MRI) is a relatively slow imaging technique because of the nature of its acquisition, which relies on exciting the spins of atoms and recording their relaxation times within a spatial encoding scheme. Nonetheless, MRI is one of the most compelling imaging modalities that has enabled advanced in-vivo analysis of brain activity and neuronal microstructure using techniques such as functional MRI and diffusion-weighted (DW)-MRI. These advanced imaging techniques require relatively long acquisitions that are, consequently, very susceptible to the subject's motion. When possible, subjects and patients are asked to stay still during MRI scans, but motion is inevitable.

Extensive research has been carried out on motion-robust sequences and motion correction techniques in MRI. However, the use of motion compensation techniques is limited by the type and amount of motion that can be compensated for, the dependency on the scanner platform and the need for pulse sequence modifications, and/or difficult setup. Accordingly, current MRI practice is still based on prevention of motion. In newborns, young children, and patients with limited cooperation, this commonly requires full sedation or general anesthesia, which is time consuming, costly, and is associated with significant risks.

SUMMARY

Some embodiments are directed to slice-level registration-based motion tracking. Correcting motion at the slice-level rather than at the volume level provides a higher temporal resolution useful for tracking motion in patients who move frequently and enables dealing with fast motion. In some aspects, slice-to-volume registration is coupled with a state-space model of motion dynamics to make the registration robust to noise and image artifacts boosting its accuracy for large motion. Some aspects use an outlier-robust Kalman filtering approach to improve the robustness of the technique to registration failures, inaccuracies, and motion-corrupted scans.

Some embodiments are directed to a computer system configured to process magnetic resonance imaging (MRI) data of an object to perform motion correction. The computer system comprises an input interface configured to receive the MRI data, wherein the MRI data comprises a three-dimensional volume of time-sequentially acquired and spatially interleaved two-dimensional slices. The computer system further comprises at least one processor programmed to estimate, for each slice of the two-dimensional slices, parameters for a state space model using a filter that predicts the location of the object for temporally adjacent slices, wherein the state space model represents motion dynamics of the object throughout acquisition of the three-dimensional volume, register each of the two-dimensional slices to a reference image based, at least in part, on the estimated parameters; and reconstruct an image based, at least in part, on the registered two-dimensional slices. The computer system further comprises an output interface configured to output the reconstructed image.

Other embodiments are directed to a method of performing motion correction of magnetic resonance imaging (MRI) data of an object, wherein the MRI data comprises a three-dimensional volume of time-sequentially acquired and spatially interleaved two-dimensional slices. The method comprises estimating, with at least one computer processor, for each slice of the two-dimensional slices, parameters for a state space model using a filter that predicts the location of the object for temporally adjacent slices, wherein the state space model represents motion dynamics of the object throughout acquisition of the three-dimensional volume, registering each of the two-dimensional slices to a reference image based, at least in part, on the estimated parameters, reconstructing an image based, at least in part, on the registered two-dimensional slices, and outputting the reconstructed image.

Other embodiments are directed to a non-transitory computer readable medium encoded with a plurality of instructions that, when executed by at least one computer, perform a method of performing motion correction of magnetic resonance imaging (MRI) data of an object, wherein the MRI data comprises a three-dimensional volume of time-sequentially acquired and spatially interleaved two-dimensional slices. The method comprises estimating, with at least one computer processor, for each slice of the two-dimensional slices, parameters for a state space model using a filter that predicts the location of the object for temporally adjacent slices, wherein the state space model represents motion dynamics of the object throughout acquisition of the three-dimensional volume, registering each of the two-dimensional slices to a reference image based, at least in part, on the estimated parameters. reconstructing an image based, at least in part, on the registered two-dimensional slices, and outputting the reconstructed image.

The foregoing summary is provided by way of illustration and is not intended to be limiting.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Some conventional motion correction techniques for MRI analysis are based on volume rejection and volume-tovolume registration. The inventors have recognized and appreciated that such motion correction techniques may be improved at least because they do not take into consideration information about motion between acquired MRI slices (inter-slice motion) or motion during acquisition of an MRI slice (intra-slice motion). To this end, some embodiments are directed to slice-level registration-based motion tracking techniques capable of compensating for fast and/or large motion.

Slice-to-volume registration has been used for motion correction of some types of MRI data, though technical challenges have generally restricted its use in motion correcting other types of MRI data such as diffusion weighted image (DWI) data. Image registration is an ill-posed problem without a guaranteed optimal solution. Slice-to-volume registration is further complicated by the limited information available in two-dimensional slices of MRI data to estimate a three-dimensional mapping to a reference volume, which may also be challenging to obtain or reconstruct for a moving subject. Often, for slice-to-volume registration to be successful, the slice has to be in close proximity to its corresponding spatial location in the coordinates of the reference volume. Accordingly, some previous techniques use multistage registration schemes to initialize slice-to-volume transformations or use parametric models to estimate relative slice positions.

Some embodiments are directed to a novel technique for slice-level motion estimation and correction in MRI. This technique employs a filtering method to track a subject's head (or other imaged object of interest) motion during scans based on registering acquired slices to a reference volume over time. Experimental results on DWI sequences showed that the technique was successful in robustly estimating head motion, rejecting motion-corrupted slices, filtering motion-corrupted data, and reconstructing diffusion tensors. Through effective processing of imaging data, this technique outperforms the state-of-the-art DWI motion correction techniques based on volume-to-volume registration; and can readily be used for retrospective analysis of motion-corrupted DWI scans or for real-time determination of motion corrupted slices during an imaging session. The technique is platform-independent in the sense that it can be used for motion-correction of DWI data obtained using different scanners and does not require a specific vendor platform, hardware setup, pulse sequence modification or prospective planning. Experimental results using the motion correction technique showed that the technique can deal with slow and fast motions across some extremes; so, depending on the goals and the imaging protocols, it may palliate the need for sedation or anesthesia, or repeated scans in newborns, young children, and patients with limited cooperation, and can significantly simplify, improve, and promote research using MRI in these populations.

Figure 1:
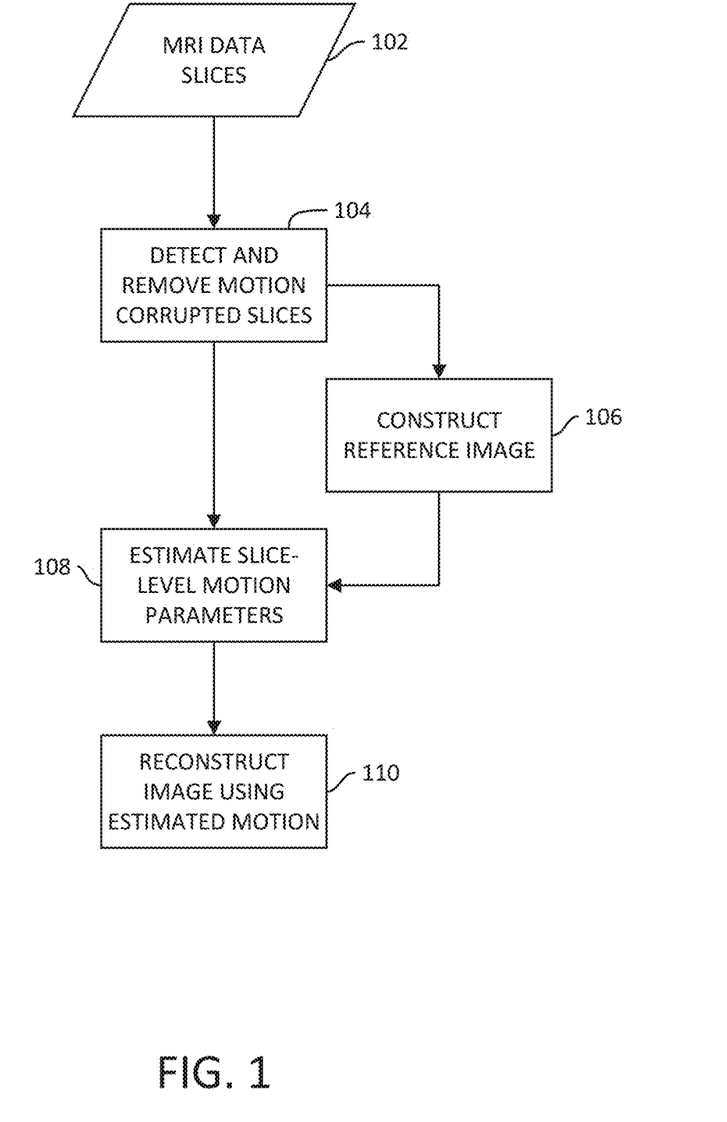
FIG. 1 illustrates a process for performing motion correction on a dataset of MRI slices in accordance with some embodiments.

FIG. 1 illustrates a process for performing motion correction on an MRI dataset (e.g., a three-dimensional volume of two-dimensional slices) in accordance with some embodiments. Throughout this disclosure, a stack or "volume" of diffusion weighted (DW) images is used as an example of the type of MR images that may be motion corrected in accordance with some embodiments. DW brain MRI, which involves relatively long duration scans with varying contrast is a particularly challenging dataset for a slice-to-volume image registration-based approach. It should be appreciated, however, that the motion correction techniques described herein may be used for processing any set of sequentially acquired 2D MR images (e.g., structural, functional or diffusion MRI) from a dynamically moving subject and embodiments are not limited in this respect.

A shown in FIG. 1, given a set of MRI data slices 102, the process proceeds to act 104, where slices corrupted by motion are identified and removed from the dataset. The process then proceeds to act 106, where a reference image is constructed. The process then proceeds to act 108, where slice-level motion parameters are estimated by registering the image slices to the reference image using the techniques described herein. The process then proceeds to act 110, where an image is reconstructed based, at least in part, on the estimated motion parameters. Each of the acts illustrated in the process of FIG. 1 is described in more detail below.

Intra-Slice Motion Estimation

Intra-slice motion at time k results in signal loss and distortion in all slices acquired at time k. When intra-slice motion is detected at time k, all slices acquired at that time may be removed from further analysis. In some conventional DW imaging sequences, a single slice is acquired at each time k. Simultaneous multi-slice (SMS) techniques enable the acquisition of multiple (e.g., typically 2-5) slices at different spatial locations at each time k. For diffusion weighted imaging, SMS acquisition is performed by interleaved 2D echo-planar imaging with $M_B$ multi-band excitations. Therefore, at the smallest time step k, k-space data is acquired for $M_B$ slices simultaneously from multiple receiver coils and is used to reconstruct slice images through unaliasing.

In accordance with some embodiments, detection of motion-corrupted slices relies on the fact that MR image slices are acquired in an interleaved manner and fast intra-slice motion occurs occasionally. MR image slices are often obtained in an interleaved order to avoid slice cross-talk and spin history artifacts. In an interleaved acquisition, adjacent slices are obtained at different time points and patient motion results in corruption of image slices independently. In this scheme, artifacts caused by motion can be identified in the out-of-plane views of an image volume in which motion-corrupted slices appear as a severe intensity discontinuity along the slice-select direction.

Some embodiments are directed to automatically identifying motion-corrupted slices, at least in part, by using image features based on inter-slice intensity discontinuity (ISID) computed using a morphological closing filter along the slice-select direction. Assuming a 3D image, I, with m slices and the image after applying the morphological closing, $I_c$, a difference image can be expressed as $\tilde{I}=I_c-I$. Having the difference image $\tilde{I}$, the median and mean intensity of slices, i.e., $\tilde{I}_k, 0 \leq k \leq m-1$, may be used to detect motion-corrupted slices. In some embodiments, an image slice is considered a corrupted image if the median intensity in the difference image is greater than zero, i.e., median($\tilde{I}_k$)>0 or the mean slice intensity in the difference image is detected as an outlier among mean intensities of all slices. The interquartile rule (IQR) for outliers may be used to detect motion-corrupted slices based on the mean slice intensity in the difference image. In some embodiments, MR volumes with more than 15% corrupted slices may be excluded from further analysis.

The inventors have recognized that some purely statistical techniques for identifying motion-corrupted slices may not work well when only slices in the acquired volume are considered in the analysis. An assumption that statistical techniques make is that the majority of the acquired data is motion free. However, for certain patient populations, such as children and elderly patients, motion may be frequent, and this assumption may not be valid. If a large number of the slices in the dataset are motion-corrupted, a statistical technique may fail to reject at least some of the motion-corrected slices because they are similar to other slices in the dataset.

In addition to the above-described rule-based statistical technique for identifying motion-corrupted slices, some embodiments identify motion-corrupted slices using, at least in part, a model that takes into consideration data other than that in the acquired volume. In accordance with such embodiments, a normalized mean intensity difference of each slice with the whole volume, and entropy of the individual slices may be used to model a support vector machine (SVM) classifier. Alternatively, a machine learning-based classifier other than a SVM classifier may be used. The machine learning-based classifier may be trained on a plurality of slices previously classified as motion-corrupted or motion-corruption free. Using a trained SVM classifier, a sensitivity of 86.6% in detecting motion-corrupted slices and 98.2% specificity was achieved in experimental results. In some embodiments, slices identified as being corrupted may be removed for both inter-slice motion estimation and image reconstruction.

Constructing a Reference Image

Slice-to-volume registration requires the selection or construction of a reference image to which each of the slices in an acquired volume is registered. For DW imaging, multiple b=0 images are often acquired along with the set of diffusion-sensitized images. In such a case, a reference image, namely $\overline{B}_0$, in an isotropic regular 3D grid may be constructed from multiple b=0 images through an iterative process.

The first b=0 volume or a b=0 image with the least amount of motion may be chosen as the initial reference image and may be registered to slices in all other b=0 image volumes using the inter-slice motion estimation technique described in more detail below. Then, an isotropic 3D image may be reconstructed in the coordinates of the selected b=0 image using image information of all b=0 images. The initial reconstructed b=0 image may not have high quality because of suboptimal motion estimation due to an imperfect initial reference image for registration; therefore, the reconstructed image may be used as a new reference for a next iteration of slice-level registration-based motion tracking. Typically two or three iterations may be needed for the algorithm to converge to obtain a high-quality $\overline{B}_0$ image for use as a reference image in the registration-based motion tracking technique described in more detail below. The image intensity at the center of the regular grid points of the $\overline{B}_0$ image may computed based on all (n) irregular points around the center grid in a 3×3×3 neighborhood using $$\overline{B}_{0,regular} = \frac{\sum_{i=1}^{n} w_i B_{0,irregular}}{\sum_{i=1}^{n} w_i} \quad (1)$$

where $w_i$ is a distance weight based on a Gaussian kernel centered at the regular grid point, computed using $$w_i = \frac{1}{\sigma\sqrt{2\pi}} e^{-1/2(r_i/\sigma)^2} \quad (2)$$

where $r_i$ is the distance between the ith point and the center of the grid point computed in the slice space to account for the slice profile, σ is the standard deviation of a bell-shaped Gaussian function, and n is the total number of points in the neighborhood. The weights $w_i$ balance the contribution of multiple observed points based on their distance to the location where the tensor is computed. In some embodiments, the value of σ=0.5.

Inter-Slice Motion Estimation

Slice-to-volume registration, used in some conventional techniques for inter-slice motion correction and image reconstruction, is often initialized by volume-to-volume registration. However, such an approach is suboptimal and is not robust. In contrast, some embodiments employ slice-level motion tracking, where image registration is used to capture the dynamics of motion. The problem is formulated as a dynamic state-space model estimation where slices, as observations, are used in image registration to estimate motion parameters considered to be the hidden states. In some embodiments in which a SMS acquisition strategy was used to acquire the data, the slice timing profile and the 3D coverage of the anatomy provided by multiple slices acquired simultaneously in the SMS acquisition is leveraged to provide more robust motion tracking.

In accordance with some embodiments, after a reference image (e.g., $\overline{B}_0$) has been constructed, the rest of the slices in the MR dataset may be transformed to the same coordinates to correct for inter-slice motion. Inter-slice motion correction in accordance with some embodiments captures dynamics of a subject's motion through slice-level image registration. Each image slice has a time stamp k, which shows the sequence of its acquisition among all t slices. In some embodiments, the dynamics of motion may be modeled using a state-space model. Assuming a finite sequence of observations $y_1, \ldots, y_t$, generated by a corresponding sequence of hidden states $x_1, \ldots, x_t$ that represent the motion, the states of a discrete-time dynamic process may be estimated. The discrete-type dynamic process is governed by a stochastic equation as $$x_k = H(x_{k-1}) + w_{k-1} \quad (3)$$

with a measurement $y_k \in \square^m$ that is $$y_k = I_S(x_k) + v_k \quad (4)$$

where $\omega_k$ and $v_k$ are process and measurement noise/disturbances and represent uncertainty in the modeling of motion dynamics and measurements, respectively. H in Eq. (3) defines motion dynamics relating the states at the previous time step k−1 to the states at the current step k in the absence of process noise. $I_S$ in Eq. (4) is a nonlinear function that relates states $x_k$ to the measurement $y_k$. In other words, $I_S(x_k)$ is the image slice corresponding to $y_k$ in the coordinates of the base 3D image, i.e., $I_V$. The observation $y_k$ can be considered as a vector of gray-scale intensities of the image slice acquired at time step k or any other information extracted from the image reflecting the motion effects. Without loss of generality, a 6-parameter rigid 3D transformation for head motion may be adopted, i.e., d=6 and x may be represented by $[\theta_x, \theta_y, \theta_z, t_x, t_y, t_z]^T$; where $t=[t_x, t_y, t_z]^T$ is the vector of translation parameters along x, y, and z axes, and $\theta=[\theta_x, \theta_y, \theta_z]$ is the vector of Euler rotation parameters about these axes.

Using the representation of motion dynamics and measurements in Eqs. (3) and (4), various linear and nonlinear state estimation techniques can be employed to obtain head motion states based on image slice information over time. In accordance with some embodiments, state estimation is integrated with slice-to-volume image registration to achieve image-based motion tracking using variants of a Kalman filter (KF) for state estimation. The Kalman filter is used to track the position of an imaged object over time as new data is acquired by the system at different time points k. Although use of a Kalman filter is described herein for modelling motion dynamics in accordance with some embodiments, it should be appreciated that any filter that models a sequence of imaged object (e.g., head) measurements to make predictions about the new position of the object may alternatively be used. For example, a non-linear filter, a particle filter, or any other physics-based model of the object may alternatively be used.

Solving the slice-to-volume registration problem is challenging if all slices are considered as independent, such that the motion between slices is arbitrary. Modeling motion dynamics using a Kalman filter for state estimation in accordance with some embodiments facilitates the image slice-to-volume registration by placing physical constraints on the motion from slice to slice rather than assuming that the motion between slices is arbitrary. For example, a patient placed on their back in an MRI scanner often moves their head in a rolling motion, and the Kalman filter takes this information into account to make predictions about the location of the head from slice to slice. The predictions are used to select a starting point for the slice registration search, which greatly improves the computational efficiency of the slice registration process.

Using the Kalman filter for state estimation, the motion dynamics in Eq. (3) can be modeled as $$x_k = x_{k-1} + \omega_{k-1} \quad (5)$$

where any change in the states from the previous time step is due to some random movement of the patient modeled by $\omega_{k-1}$. Given that $y_k$ in Eq. (4) is a vector of gray-scale intensities of the acquired image slice, the output model of $I_S(x_k)$ will be highly nonlinear. Nonlinear state estimation methods are not as widely available as their linear counterparts and are often difficult to implement and robustly tune the parameters. Hence, in some embodiments, the nonlinear output model is separated from the filtering process and Eq. (4) is rewritten as $$z_k = x_k + v_k = \underset{p}{\mathrm{argmax}} f(I_s(p), y_k) \quad (6)$$

in which f ($I_S$ (p), $y_k$) is a similarity metric between the image slice acquired at time step k, i.e., $y_k$ (image measurement vector), and the corresponding slice in the base 3D volume that is rigidly transformed with parameters p (i.e., $I_S(p)$). Therefore, the base 3D volume may first be registered to the slice acquired at time step k, and the resulting Euler transformation parameters may be used as the measurement vector for the Kalman filtering process to estimate motion parameters. In this formulation, $v_k$ represents uncertainties in the estimation of the rigid head motion parameters based on slice-to-volume registration.

Filter-based inter-slice motion estimation in accordance with some embodiments provides several advantages over conventional motion correction techniques. The slice-to-volume registration is initialized at time step k based on the states estimated at time step k−1, i.e., $\hat{x}_{k-1}$. Considering that the time step between slice acquisitions is about 100 ms for DW imaging, which is relatively fast compared to the scale of subject movements, the initialization puts each slice in a very close proximity to the corresponding spatial locations of the 3D image volume. This increases the success rate of the registration process and enables slice-level registration-based motion tracking. Additionally, some embodiments use an outlier-robust Kalman filter (ORKF) for motion estimation, which accounts for noisy measurements caused by motion-corrupted slices and registration failures. Noisy measurements may occur when fast subject motion results in through-plane motion artifacts or when slice-to-volume registration fails in the boundary of the imaged anatomy due to the lack of sufficient image features. Similar to the classical Kalman filter, ORKF assumes that the process noise has a Gaussian distribution with a fixed covariance matrix Q (i.e., $\omega_k \Box N$ (0,Q)); but unlike the classical Kalman filter, that assumes measurements are also corrupted by additive white Gaussian noise with a fixed covariance matrix R (i.e., $v_k \Box N$ (0,R)), the ORKF allows more flexible modeling of uncertainties in measurements in which the noise level may vary over time or the noise may have a heavier tail than the Gaussian distribution. The covariance of the measurement noise is therefore not fixed a priori and changes based on the sequential observations over time. The distribution of the measurement noise can be defined as $$v_k \Box N(0, S_k) \quad (7)$$

in which $S_k$ is the covariance of the measurement noise at time step k, sampled from a probability distribution as $$S_k^{-1} \Box W\left(\frac{R^{-1}}{s}, s\right) \quad (8)$$

where W ($\Lambda$, s) denotes a Wishart distribution with a d×d precision matrix $\Lambda \succ 0$ and s>d>1 degrees of freedom. The prior mean of W ($\Lambda$, s) is s$\Lambda$ where s quantifies the concentration of the distribution around its mean. With the definition of the measurement noise model in Eqs. (7) and (8), the state estimation problem for motion tracking is robust to outliers.

Algorithm 1, represented below, shows a pseudo-code implementation of the outlier-robust slice-level registration-based motion estimation in accordance with some embodiments.

---

Algorithm 1 Pseudo-code of the ORKF-based motion estimation for each slice. $\hat{x}_k^-$ is the a priori estimate of the states at time step k given knowledge of the process prior to that time. $\hat{x}_k$ is the a posteriori estimate of the states at time step k given measurement $z_k$. $P_k^-$ and $P_k$ are a priori and a posteriori estimates of the error covariance, respectively. $K_k$ is the Kalman gain. Q and R are the covariance of the process and measurement noise, respectively.

Input: $I_V$, $y_k$, $\hat{x}_{k-1}$
Output: $\hat{x}_k$
1: slice-to-volume registration:

2: $z_k \leftarrow \underset{p}{\max}$ f ($I_S(p)$, $y_k$); $p_0 = \hat{x}_{k-1}$ 3: predict states:
4: $\hat{x}_k^- \leftarrow \hat{x}_{k-1}$, $\hat{x}_k \leftarrow \hat{x}_k^-$
5: $P_k^- \leftarrow P_{k-1} + Q$, $P_k \leftarrow P_k^-$
6: repeat
7:    update noise:
8:    $\delta = z_k - \hat{x}_k$
9:    $\Lambda_k = (sR + \delta\delta^T + P_k)/(s + 1)$
10:   update states:
11:   $K_k = (P_k^- + \Lambda_k)^{-1} P_k^-$
12:   $\hat{x}_k = \hat{x}_k^- + K_k^T(z_k - \hat{x}_k^-)$
13:   $P_k = K_k^T \Lambda_k K_k + (I - K_k)^T P_k^-(I - K_k)$

```
14: until converged
15: return x̂_k
```

As illustrated in Algorithm 1, each slice in the acquisition order is first registered to the reference volume to compute $z_k$. The registration is initialized based on the estimated motion in the previous time step, i.e., $\hat{x}_{k-1}$. Then, motion states are computed in an iterative algorithm to compute $\hat{x}_k$ based on $z_k$. The process of motion estimation using the algorithm is applied in two stages on b=0 and diffusion-sensitized (b≠0) images, separately. First, motion estimation is applied to images to reconstruct a motion-free isotropic 3D base image shown by $\overline{B}_0$. In the second stage, the reconstructed base b=0 image ($\overline{B}_0$) is used as the reference volume for motion tracking, where it is registered to the diffusion-sensitized image slices.

Image Reconstruction

Estimated motion parameters for each diffusion-sensitized image slice enable all of the MRI data to be transformed to the same coordinates for performing further analysis. The particular image reconstruction process used is dependent on the type of image data acquired. In the example described below, DW image data is reconstructed, though it should be appreciated that other types of MR data may also be reconstructed using other techniques based, at least in part, on the estimated motion parameters. Although more complex models of the diffusion signal could be considered to benefit from motion correction, for the sake of simplicity, and to focus on the effect of motion correction, reconstruction of the diffusion tensor matrix based on the Stejskal-Tanner (ST) equation is considered in accordance with some embodiments. Having a base $\overline{B}_0$ image and $N_{b \neq 0}$ diffusion-sensitized volumes, a diffusion tensor can be estimated at any point of the regular grid in $\overline{B}_0$ by solving ST equation as $$B_{i,regular} = \overline{B}_{0,regular} e^{-b g_i^T D g_i}, \quad 1 \leq i \leq N_{b \neq 0} \quad (9)$$

where $\overline{B}_{0,regular}$ is the intensity at the regular grid location in $\overline{B}_0$, and $B_{i,regular}$ is the corresponding intensity at the ith diffusion-sensitized image; $g_i = [g_{ix}, g_{iy}, g_{iz}]$ represents the ith diffusion gradient direction in the $\overline{B}_0$ coordinates and b is an imaging sequence dependent constant, which specifies the diffusion sensitivity. Furthermore, D is a 3×3 symmetric positive definite matrix representing a diffusion tensor expressed in $\overline{B}_0$ coordinates with elements that are then rearranged in a parameter vector $\gamma = [D_{xx}, D_{xy}, D_{xz}, D_{yy}, D_{yz}, D_{zz}]$. Given n>6 diffusion-sensitized images with non-collinear gradient directions and a constant b-value, diffusion tensors can be estimated by minimizing an objective function as $$f(\gamma) = \frac{1}{2} \sum_{i=1}^{n} \alpha_i^2 \left( \ln\left(\frac{B_{i,regular}}{\overline{B}_{0,regular}}\right) - \sum_{j=1}^{6} M_{i,j} \gamma_j \right)^2 \quad (10)$$

where $n = N_{b \neq 0}$, and $$M = -b \begin{bmatrix} g_{1x}^2 & 2g_{1x}g_{1y} & 2g_{1x}g_{1z} & g_{1y}^2 & 2g_{1y}g_{1z} & g_{1z}^2 \\ \vdots & \vdots & \vdots & \vdots & \vdots & \vdots \\ g_{nx}^2 & 2g_{nx}g_{ny} & 2g_{nx}g_{nz} & g_{ny}^2 & 2g_{ny}g_{nz} & g_{nz}^2 \end{bmatrix} \quad (11)$$

is an n×6 matrix. Moreover, $\alpha_i$s are weights for different gradient directions in the objective function. In some embodiments, the observed diffusion weighted signals may be used as weights in the computation of diffusion tensors using a weighted linear least square (WLLS) method. For example, $\alpha_i = B_{i,regular}$ may be used in Eq. (10). By definition of the design matrix of Eq. (11), the diffusion tensor matrix (D) is not guaranteed to be positive definite, although it is symmetric. A typical solution is to use the Cholesky factorization to define $D = U^T U$, where U is an upper triangular matrix with non-zero diagonal elements. Estimating elements of U guarantees a positive definite D.

In order to compute diffusion tensors using Eq. (10), image intensities of the diffusion-sensitized images at the regular grid locations identical to those of the $\overline{B}_0$ image are typically required. However, in some embodiments, due to motion correction, diffusion-sensitized image intensities are available at some irregularly sampled points in the 3D space of the imaged anatomy. To estimate diffusion tensors from these motion-corrected DWI slices, some embodiments directly reconstruct diffusion tensors at regular grid points using data from motion-corrected irregular point locations. To this end, a data structure of motion-corrected point locations and their properties around any regular grid point in a local neighborhood is formed. Each data point in the data structure is characterized by its position in the $\overline{B}_0$ coordinates, a gray-scale value, b value and a vector of diffusion gradient directions.

Similar to Eq. (10), given n>6 diffusion-sensitized points with noncollinear gradient directions, diffusion tensors may be computed by minimizing the following objective function $$f(\gamma) = \frac{1}{2} \sum_{i=1}^{n} w_i^2 \alpha_i^2 \left( \ln\left(\frac{B_{i,regular}}{\overline{B}_{0,regular}}\right) - \sum_{j=1}^{6} M_{i,j} \gamma_j \right)^2 \quad (12)$$

where $\alpha_i = B_{i,irregular}$, $B_{i,irregular}$ is the observed diffusion-sensitized signal (gray-scale value) at any motion-corrected point location, and $\overline{B}_0$ is the corresponding non-diffusion weighted signal, which is interpolated from the $\overline{B}_0$ image at that irregular point location. Finally, $w_i$ is a weighting factor that is computed as $$w_i = \frac{1}{\sigma \sqrt{2\pi}} e^{-1/2 (r_i/\sigma)^2} \quad (13)$$

where $r_i$ is the distance between the ith point and the center of the grid point computed in the slice space to account for the slice profile; $\sigma$ is the standard deviation of a bell-shaped Gaussian function, and n is the total number of points in the neighborhood. The weights ($w_i$s) balance the contribution of multiple observed points based on their distance to the location where the tensor is computed.

Gradient directions recorded in diffusion-sensitized images are in the scanner coordinates. In order to compute the gradient directions in the $\overline{B}_0$ coordinates in Eq. (9), not only the orientation of the acquired image with respect to the scanner coordinates should be considered, but also the estimated rotation for each slice with respect to the coordinates from the motion estimation step should be applied. Assuming $R_0$ is the rotation matrix obtained from the image volume orientation and $R_m$ is the rotation matrix estimated for each slice through the slice-to-volume registration-based motion tracking, the diffusion gradient direction for each slice in the $\overline{B}_0$ coordinates, i.e., $g_i$ in Eq. (9) is calculated as $$g_i = R_m R_0^{-1} g_{0i} \quad (14)$$

where $g_{0i}$ is the vector of the ith predefined gradient direction in the scanner coordinates.

Illustrative Application of Motion Tracking

Figure 2:
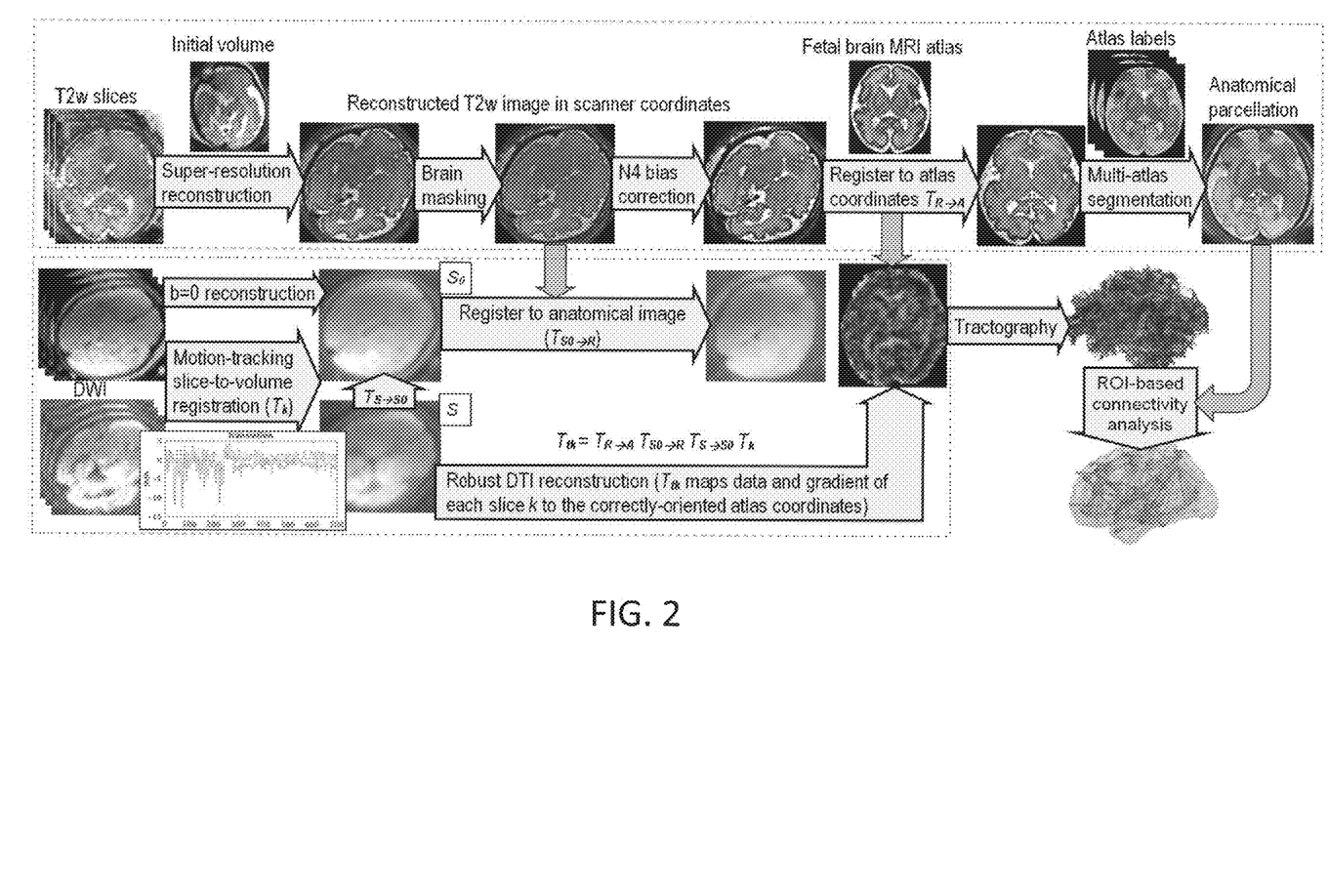
FIG. 2 illustrates an application of a motion correction process, in accordance with some embodiments, to process fetal brain diffusion tensor imaging data.

FIG. 2 shows an example processing pipeline for motion-robust fetal brain diffusion tensor imaging (DTI) reconstruction and structure connectivity analysis in accordance with some embodiments. The two dashed-line boxes in the FIG. 2 separate the T2w image processing pipeline (on top) from the DWI processing pipeline (on the bottom). A volumetric T2w image with isotropic resolution of 0.7 mm$^3$ was reconstructed from multiple stacks of T2w scans using robust super-resolution volume reconstruction. An approximate ellipsoidal brain mask was used to crop the brain region prior to reconstruction, but a precise manual brain mask was obtained after reconstruction. The brain mask was then used in N4 correction of intensity non-uniformity. The corrected masked image was registered to the atlas space and tissue segmentation and anatomical parcellation was obtained from multiatlas segmentation using label propagation through deformable registration and probabilistic label fusion. A spatiotemporal fetal brain MRI atlas with anatomical parcellations was used in this process. The DWI stacks of slices are processed in accordance with the motion correction techniques described above. Through the combination of the rigid transformations computed throughout this pipeline, the DWI data were mapped into the S0 image for the reconstruction of DTI in standard orientation. This allowed for standard color-coding of FA and tractography and enabled groupwise connectivity analysis.

Figure 3:
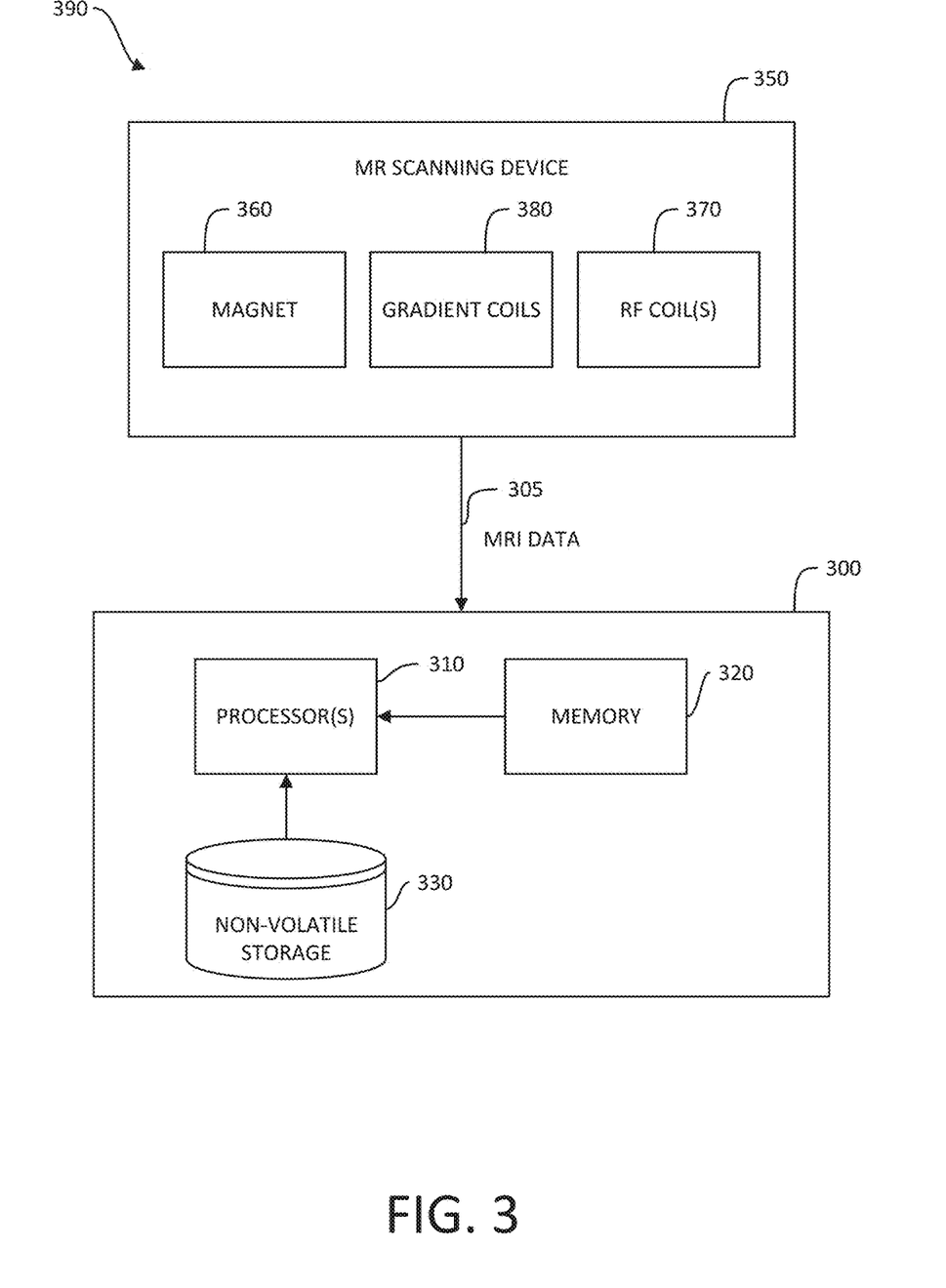
FIG. 3 illustrates a computer-based system on which some embodiments may be implemented.

FIG. 3 illustrates a block diagram of one embodiment of a system 390 suitable for practicing various techniques described herein. System 390 comprises a magnetic resonance (MR) scanning device 350 and computer system 300. MR scanning device 350 may be any device capable of obtaining MR data and, in particular, capable of acquiring diffusion weighted image data. For example, MR scanning device 350 may include a magnet 360 capable of producing a magnetic field of desired strength, and may produce a uniform or gradient magnetic field. Magnet 360 may be of any shape, size and strength and may include multiple magnets of any size, shape and strength.

MR scanning device 350 also comprises one or more RF coils 370 arranged proximate the magnet and adapted to provide RF pulse sequences to an object being scanned and/or to detect NMR signals (e.g., gradient-echo signals) emitted therefrom. RF coils 370 may comprise one or multiple coils arranged in any configuration to perform single coil acquisition or multiple coil acquisition (i.e., parallel MR). RF coils 370 may include independent RF coils for providing RF pulse sequences (excitation coils) and detecting NMR signals (receive coils), or one or more RF coils may be arranged as both an excitation and receive coils.

MR scanning device 350 also comprises a plurality of gradient coils configured to enable encoding of frequency and/or phase in one or more of the x-direction, y-direction, and z-direction. Any configuration of magnet 360, RF coil(s) 370, and gradient coils 380 may be suitable, as the techniques described herein are not limited for use on data obtained from any particular MR scanning device.

Computer system 300 may be used to implement one or more techniques described herein. Computer system 300 may include one or more processors 310 and one or more non-transitory computer-readable storage media (e.g., memory 320 and one or more non-volatile storage media 330). The processor 310 may control writing data to and reading data from the memory 320 and the non-volatile storage device 330 in any suitable manner. Processor 310, for example, may be a processor on any device, for example, a personal computer, a workstation, one or more servers, or may be a processor on-board or otherwise integrated with MR scanning device 350, etc.

In some embodiments, processor(s) 310 is configured to perform, during a scanning session, one or more of the motion correction techniques described herein on MR images acquired by MR scanning device 350. When motion correction analysis is performed during a scanning session, the quality of the acquired MR data can be monitored and additional data can be acquired and/or missing data can be reacquired to ensure a sufficient quality of the data. For example, MR slices determined to be corrupted by motion in accordance with the techniques described herein may be reacquired to improve the quality of the acquired image volume.

To perform functionality and/or techniques described herein, the processor(s) 310 may execute one or more instructions stored in one or more computer-readable storage media (e.g., the memory 320, storage media, etc.), which may serve as non-transitory computer-readable storage media storing instructions for execution by processor(s) 310. Computer system 300 may also include any other processor, controller, or control unit needed to route data, perform computations, perform I/O functionality, etc. For example, computer system 300 may include any number and type of input functionality to receive data and/or may include any number and type of output functionality to provide data, and may include control apparatus to perform I/O functionality.

Computer system 300 may be integrated into MR scanning device 350 or may be a separate stand-alone computer system, either proximate to or remote from MR scanning device 350. For example, computer system 300 may be connected to MR scanning device 350 over a network, connected to multiple scanning devices or may not be connected to any scanning device at all. When computer system 300 is connected to or integrated with MR scanning device 350, computer system 300 may be programmed to control the RF coil(s) according to a desired RF sequence or protocol, or MR scanning device 350 may have a separate controller to perform excitation and acquisition.

When computer system 300 is separate from MR scanning device 350, computer system 300 may operate on MR data previously stored on computer system 300, may obtain MRI data from some other location, e.g., another computer system, over a network, or may obtain the MRI data via transportable storage medium, etc. It should be appreciated that any computing environment may be used, as the techniques described herein are not limited for use with a computer system of any particular type or implementation.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, a tape, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A computer system configured to process magnetic resonance imaging (MRI) data of an object to perform motion correction, the computer system comprising:
    an input interface configured to receive the MRI data, wherein the MRI data comprises a three-dimensional volume of time-sequentially acquired and spatially interleaved two-dimensional slices;
    at least one processor programmed to:
        identify based, at least in part, on at least one two-dimensional slice in the three-dimensional volume and a model trained on labeled MRI data, one or more of the two-dimensional slices in the three-dimensional volume that are motion corrupted;
        estimate, for each slice of the two-dimensional slices that is not identified as being motion corrupted, parameters for a state space model using a filter that predicts the location of the object for temporally adjacent slices, wherein the state space model represents motion dynamics of the object throughout acquisition of the three-dimensional volume, wherein estimating the parameters is performed only on two-dimensional slices that are not identified as being motion corrupted;
        register each of the two-dimensional slices to a reference image based, at least in part, on the estimated parameters; and
        reconstruct an image based, at least in part, on the registered two-dimensional slices; and
    an output interface configured to output the reconstructed image.

2. The computer system of claim 1, wherein the filter is a Kalman filter.

3. The computer system of claim 1, wherein the filter is an outlier-robust Kalman filter.

4. The computer system of claim 1, wherein registering each of the two-dimensional slices to a reference image comprises using the estimated state space model parameters for a slice to select a starting point for a slice registration search process.

5. The computer system of claim 1, wherein the model is a model trained based, at least in part, using a machine learning technique.

6. The computer system of claim 1, wherein the at least one processor is further programmed to construct the reference image based, at least in part, on a plurality of images acquired in a first state, and wherein the two-dimensional slices are acquired in one or more second states different from the first state.

7. The computer system of claim 1, wherein constructing the reference image based, at least in part, on a plurality of images comprises constructing the reference image based, at least in part on an estimation of motion of the object between the plurality of images.

8. The computer system of claim 1, wherein at least two of the two-dimensional slices corresponding to different spatial locations in the three-dimensional volume were acquired at the same time.

9. A method of performing motion correction of magnetic resonance imaging (MRI) data of an object, wherein the MRI data comprises a three-dimensional volume of time-sequentially acquired and spatially interleaved two-dimensional slices, the method comprising:
    identifying based, at least in part, on at least one two-dimensional slice in the three-dimensional volume and a model trained on labeled MRI data, one or more of the two-dimensional slices in the three-dimensional volume that are motion corrupted;

estimating, with at least one computer processor, for each slice of the two-dimensional slices that is not identified as being motion corrupted, parameters for a state space model using a filter that predicts the location of the object for temporally adjacent slices, wherein the state space model represents motion dynamics of the object throughout acquisition of the three-dimensional volume wherein estimating the parameters is performed only on two-dimensional slices that are not identified as being motion corrupted;

registering each of the two-dimensional slices to a reference image based, at least in part, on the estimated parameters;

reconstructing an image based, at least in part, on the registered two-dimensional slices; and outputting the reconstructed image.

10. The method of claim 9, wherein registering each of the two-dimensional slices to a reference image comprises using the estimated state space model parameters for a slice to select a starting point for a slice registration search process.

11. The method of claim 9, wherein the model is a model trained based, at least in part using a machine learning technique.

12. The method of claim 9, further comprising:
constructing the reference image based, at least in part, on a plurality of images acquired in a first state, and wherein the two-dimensional slices are acquired in one or more second states different from the first state, wherein constructing the reference image based, at least in part, on a plurality of images comprises constructing the reference image based, at least in part on an estimation of motion of the object between the plurality of images.

13. A non-transitory computer readable medium encoded with a plurality of instructions that, when executed by at least one computer, perform a method of performing motion correction of magnetic resonance imaging (MRI) data of an object, wherein the MRI data comprises a three-dimensional volume of time-sequentially acquired and spatially interleaved two-dimensional slices, the method comprising:

identifying based, at least in part, on at least one two-dimensional slice in the three-dimensional volume and a model trained on labeled MRI data, one or more of the two-dimensional slices in the three-dimensional volume that are motion corrupted;

estimating, with at least one computer processor, for each slice of the two-dimensional slices that is not identified as being motion corrupted, parameters for a state space model using a filter that predicts the location of the object for temporally adjacent slices, wherein the state space model represents motion dynamics of the object throughout acquisition of the three-dimensional volume wherein estimating the parameters is performed only on two-dimensional slices that are not identified as being motion corrupted;

registering each of the two-dimensional slices to a reference image based, at least in part, on the estimated parameters;

reconstructing an image based, at least in part, on the registered two-dimensional slices; and outputting the reconstructed image.

14. The non-transitory computer readable medium of claim 13, wherein the filter is a Kalman filter.

15. The non-transitory computer readable medium of claim 13, wherein registering each of the two-dimensional slices to a reference image comprises using the estimated state space model parameters for a slice to select a starting point for a slice registration search process.

16. The non-transitory computer readable medium of claim 13 wherein the model is a model trained based, at least in part using a machine learning technique.

17. The non-transitory computer readable medium of claim 13, wherein the method further comprises:
constructing the reference image based, at least in part, on a plurality of images acquired in a first state, and wherein the two-dimensional slices are acquired in one or more second states different from the first state, wherein constructing the reference image based, at least in part, on a plurality of images comprises constructing the reference image based, at least in part on an estimation of motion of the object between the plurality of images.

* * * * *